(12) United States Patent
Huang et al.

(10) Patent No.: US 11,780,824 B2
(45) Date of Patent: Oct. 10, 2023

(54) PROCESS FOR PREPARING OSIMERTINIB OR A SALT THEREOF

(71) Applicant: ScinoPharm Taiwan, Ltd., Tainan (TW)

(72) Inventors: Kuan-Hsun Huang, Tainan (TW); Chung-Yang Huang, Tainan (TW); Tsung-Cheng Hu, Tainan (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 160 days.

(21) Appl. No.: 17/123,556

(22) Filed: Dec. 16, 2020

(65) Prior Publication Data
US 2022/0185794 A1   Jun. 16, 2022

(51) Int. Cl.
C07C 303/32 (2006.01)
C07C 309/04 (2006.01)
(Continued)

(52) U.S. Cl.
CPC ............ C07D 403/04 (2013.01); B01J 23/44 (2013.01); C07C 303/32 (2013.01); C07C 309/04 (2013.01)

(58) Field of Classification Search
None
See application file for complete search history.

(56) References Cited

FOREIGN PATENT DOCUMENTS

| CN | 106967050 A | 7/2017 |
| CN | 107188888 A * | 9/2017 |

(Continued)

OTHER PUBLICATIONS

Patent No. CN108623567A, machine translation, Oct. 2018, pp. 1-12 (Year: 2018).*

(Continued)

*Primary Examiner* — Medhanit W Bahta
(74) *Attorney, Agent, or Firm* — Mintz, Levin, Cohn, Ferris, Glovsky and Popeo, P.C.

(57) ABSTRACT

Provided herein are improved processes and methods for preparing osimertinib or a salt thereof, in particular osimertinib mesylate. The improved process removes the necessity of isolating the unstable aniline intermediate of formula (III) and enables the direct coupling to form the amide product of formula (II):

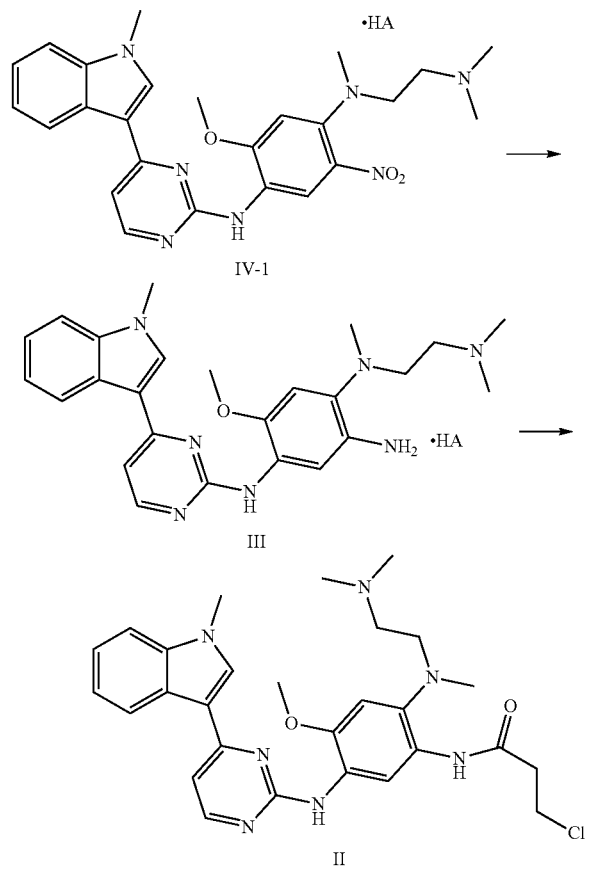

The present invention is suitable for a large-scale production, avoiding the isolation of unstable intermediate, thereby providing osimertinib or a mesylate salt thereof in both high yields and high purity.

19 Claims, 3 Drawing Sheets

(51) Int. Cl.
    *C07D 403/04*     (2006.01)
    *B01J 23/44*     (2006.01)

(56) References Cited

FOREIGN PATENT DOCUMENTS

| | | | | | |
|---|---|---|---|---|---|
| CN | 107954989 | A | * | 4/2018 | |
| CN | 108623567 | A | * | 10/2018 | |
| CN | 111303123 | A | | 6/2020 | |
| WO | 2013014448 | A1 | | 1/2013 | |
| WO | 2017134051 | A1 | | 8/2017 | |
| WO | WO-2017134051 | A1 | * | 8/2017 | ........... A61K 31/506 |
| WO | WO-2019022485 | A1 | * | 1/2019 | ........... A61K 31/506 |

OTHER PUBLICATIONS

International Search Report and Written Opinion for International PCT Application No. PCT/SG2021/050785 dated Apr. 14, 2022 (13 pages).
Finlay, R. et al. "Discovery of a Potent and Selective EGFR Inhibitor (AZD9291) of Both Sensitizing and T790M Resistance Mutations that Spares the Wild Type Form of the Receptor" J. Med. Chem. 2014, 57, 8249-8267.

* cited by examiner

Scheme 1

Scheme 2

Scheme 3

PROCESS FOR PREPARING OSIMERTINIB OR A SALT THEREOF

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Osimertinib (AZD9291, trade name Tagrisso) is the first approved medicine used to treat patients having metastatic epidermal growth factor receptor (EGFR) T790M mutation-positive non-small cell lung cancer (NSCLC). Osimertinib was approved for the indicated use under FDA's accelerated approval process based on tumor response rate and duration of response. Osimertinib is also used as a first-line treatment for patients with metastatic EGFR L858R mutation-positive or exon 19 deletion-positive NSCLC, which must be detected by an FDA-approved test. Tagrisso is sold in the form of 40 mg and 80 mg tablets. Each tablet contains 47.7 mg osimertinib mesylate (equivalent to 40 mg osimertinib) or 95.4 mg osimertinib mesylate (equivalent to 80 mg osimertinib). Tagrisso tablets also contain various inactive ingredients including microcrystalline cellulose, mannitol, low-substituted hydroxpropyl cellulose, and sodium stearyl fumarate.

The synthesis of osimertinib has been challenging and costly due to multiple functional groups present in the chemical structure. Two major synthetic methods have been reported in the art for the preparation of osimertinib or a mesylate thereof.

The first approach is disclosed in *J. Med. Chem.* 2014, 57, 8249-8267, as outlined in Scheme 1 of FIG. 1. Accordingly, the synthesis of compound 3 requires 2-pentanol as the solvent, which is highly expensive. Furthermore, microwave heating is also required for converting compound 3 to compound 4, which is not suitable for a large-scale manufacturing operation. Moreover, the reduction of the nitro group in compound 4 by Fe/ammonium chloride is environmentally hazardous and difficult to handle in a production plant. Finally, the amidation of compound 5 with acryloyl chloride is inefficient in a low isolated yield of 39%.

An improved process is disclosed in WO 2013/014448 A1, as shown in Scheme 2 of FIG. 2. First, the microwave heating for converting compound 3 to compound 4 is replaced by using i-Pr$_2$NEt in DMAc allowing for easy scaling up to a several-hundred-milligram scale. In addition, the amidation of compound 5 using 3-chloropropionyl chloride provides compound 6, which then undergoes elimination in the presence of Et$_3$N to afford osimertinib. Even though the conversion of compound 5 to osimertinib requires two steps (vs. one step), the overall yield is improved from 39% to 89%.

To address issues arising from the reduction of the nitro group in compound 4 with Fe/ammonium chloride, an improved process by means of hydrogenation is disclosed in WO 2017/134051 A1, as shown in Scheme 3 of FIG. 3. This improved process has allowed the production feasible on a large scale while avoiding iron-based residuals that would remain in the reaction mixture.

In view of the foregoing, there remains a need for an improved process to produce osimertinib or a salt thereof, in particular osimertinib mesylate, with commercially acceptable yields, increased efficiency, and less toxic chemicals.

BRIEF SUMMARY OF THE INVENTION

In a first aspect, the present disclosure provides a process for preparing osimertinib represented by formula (I):

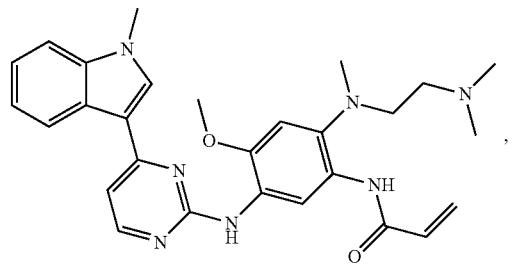

or a salt thereof, the process including:

2a) contacting a compound represented by formula (IV-1):

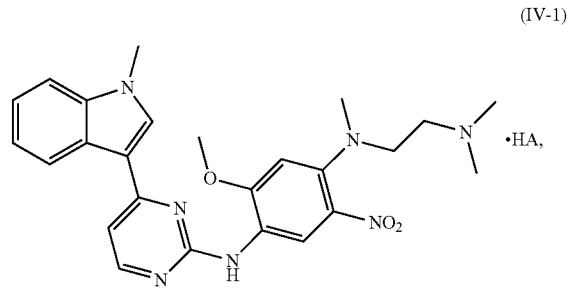 [SMILES: COc1cc(N(C)CCN(C)C)c([N+](=O)[O-])cc1Nc1nccc(-c2cn(C)c3ccccc23)n1]

with a hydrogen source and a transition-metal catalyst in a first solvent to form a compound represented by formula (III):

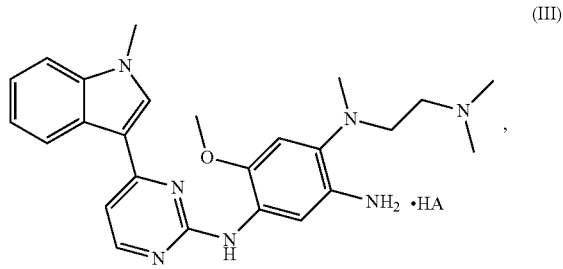

2b) reacting the compound of formula (III) with 3-chloropropionyl chloride and a first base to form a compound represented by formula (II):

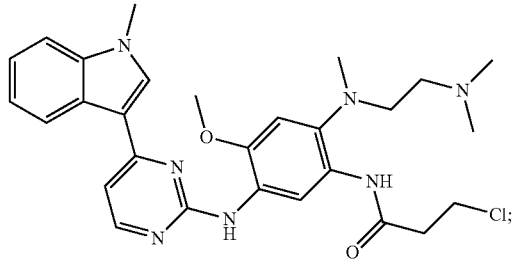

3) converting the compound of formula (II) to osimertinib of formula (I); and
4) optionally converting osimertinib of formula (I) to a salt thereof, wherein HA is an acid addition salt in each of the compound of formula (III) and the compound of formula (IV-1); and steps 2a) and 2b) are conducted in one-pot.

In a second aspect, the present disclosure provides a process for preparing osimertinib represented by formula (I):

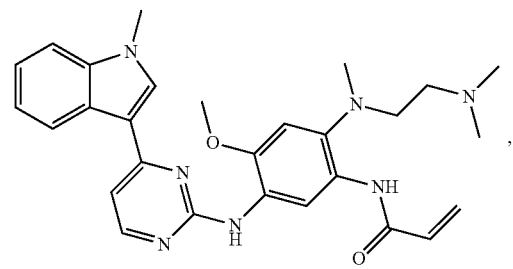

or a mesylate salt thereof, the process including:
1) contacting a compound of formula (IV):

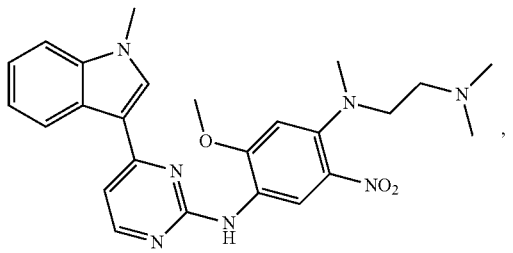

with $CH_3SO_3H$ in ethanol to form a compound represented by formula (IV-1a):

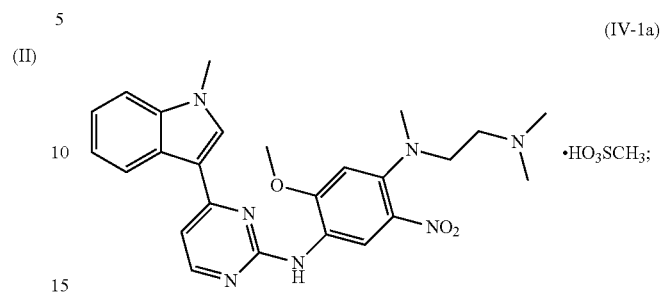

2a) hydrogenating the compound of formula (IV-1a) with a hydrogen gas and Pd(0) on carbon in ethanol to form a compound represented by formula (III-1a):

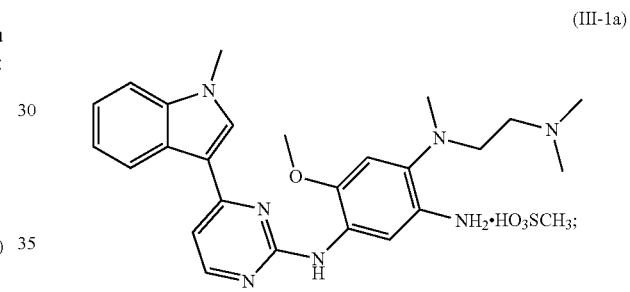

2b) reacting the compound of formula (III-1a) with 3-chloropropionyl chloride and $NaHCO_3$ in ethanol and water to form a compound represented by formula (II):

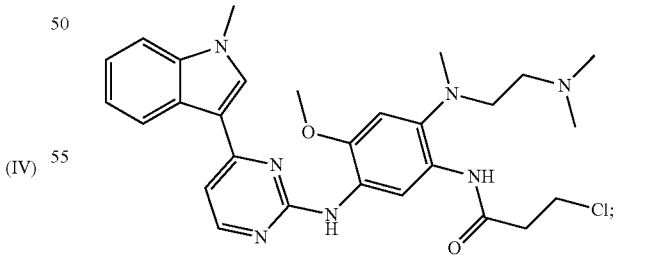

3) treating the compound of formula (II) with trimethylamine in acetonitrile to provide osimertinib of formula (I); and
4) optionally converting osimertinib of formula (I) with $CH_3SO_3H$ to a mesylate salt thereof, wherein steps 2a) and 2b) are conducted in one-pot.

In a third aspect, the present disclosure provides a compound, represented by formula (IV-1a):

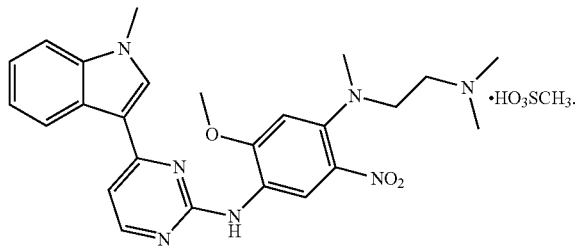

(IV-1a)

In a fourth aspect, the present disclosure provides a compound, represented by formula (III-1a):

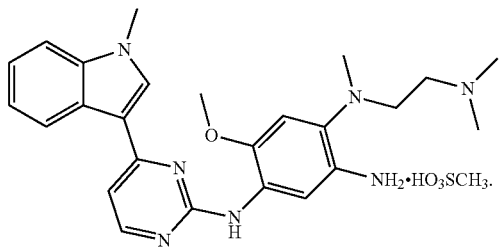

(III-1a)

DETAILED DESCRIPTION OF THE INVENTION

I. General

The present disclosure relates to an improved process for preparing osimertinib or a salt thereof, in particular osimertinib mesylate. The improved process is useful for manufacturing osimertinib or a mesylate thereof used in the development of a pharmaceutical composition containing the same.

Figure 1:
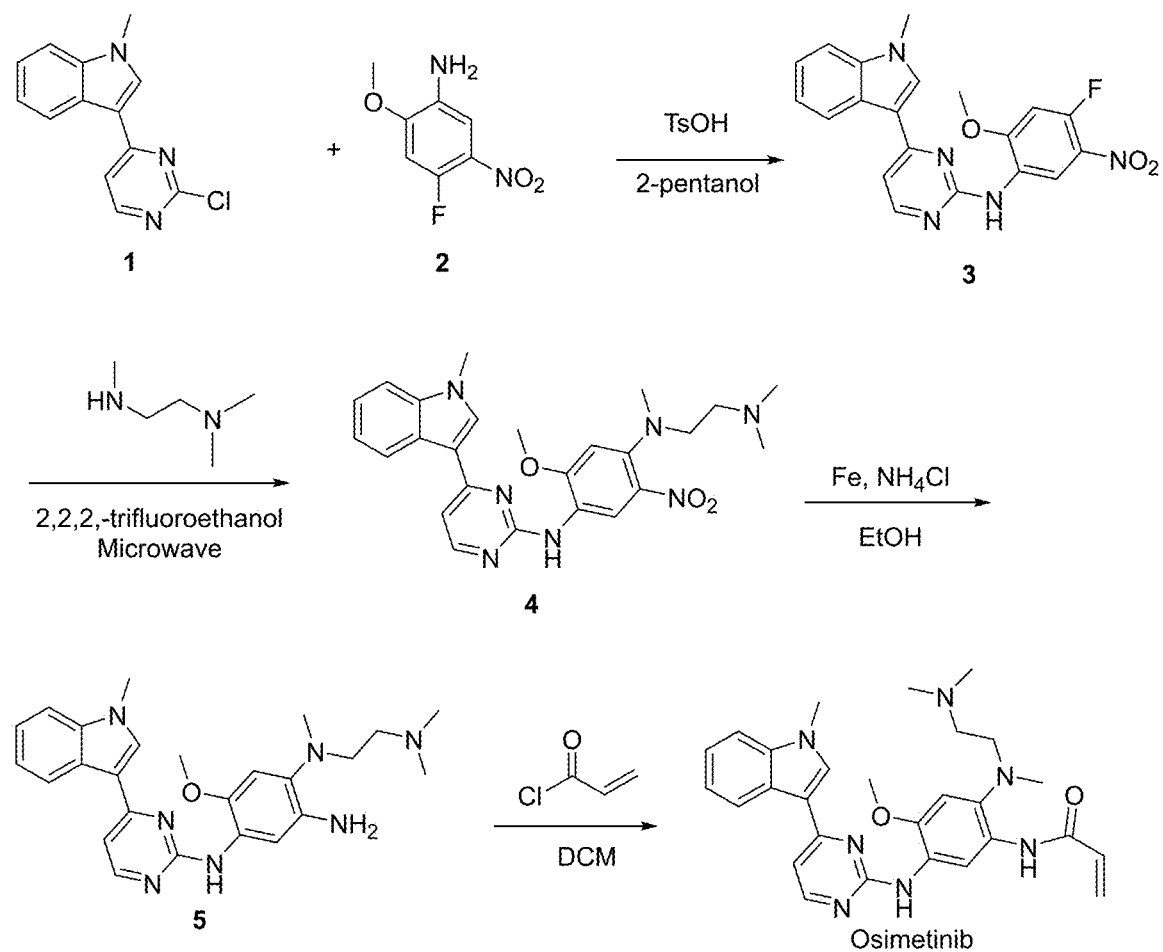
FIG. 1 shows the synthesis scheme for preparing osimertinib as disclosed in *J. Med. Chem.* 2014, 57, 8249-8267.
Figure 2:
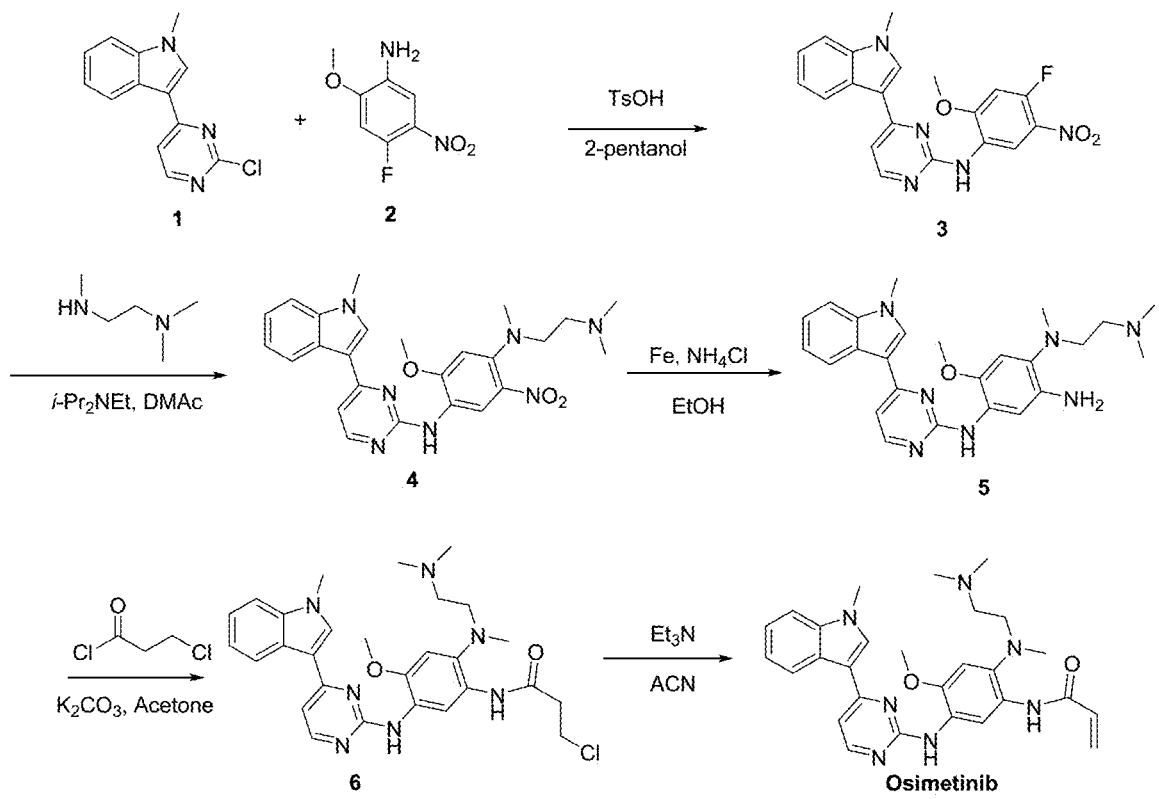
FIG. 2 shows the synthesis scheme for preparing osimertinib as disclosed in WO 2013/014448 A1.
Figure 3:
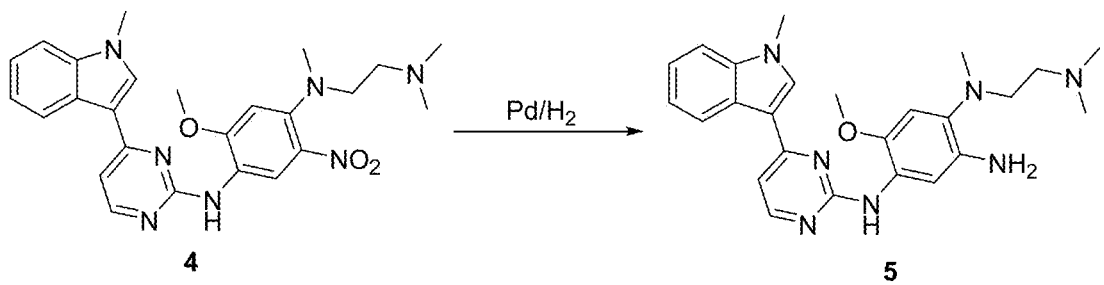
FIG. 3 shows the conversion of nitrodiamine (4) to aniline (5) by hydrogenation as disclosed in WO 2017/134051A1.
Figure 4:
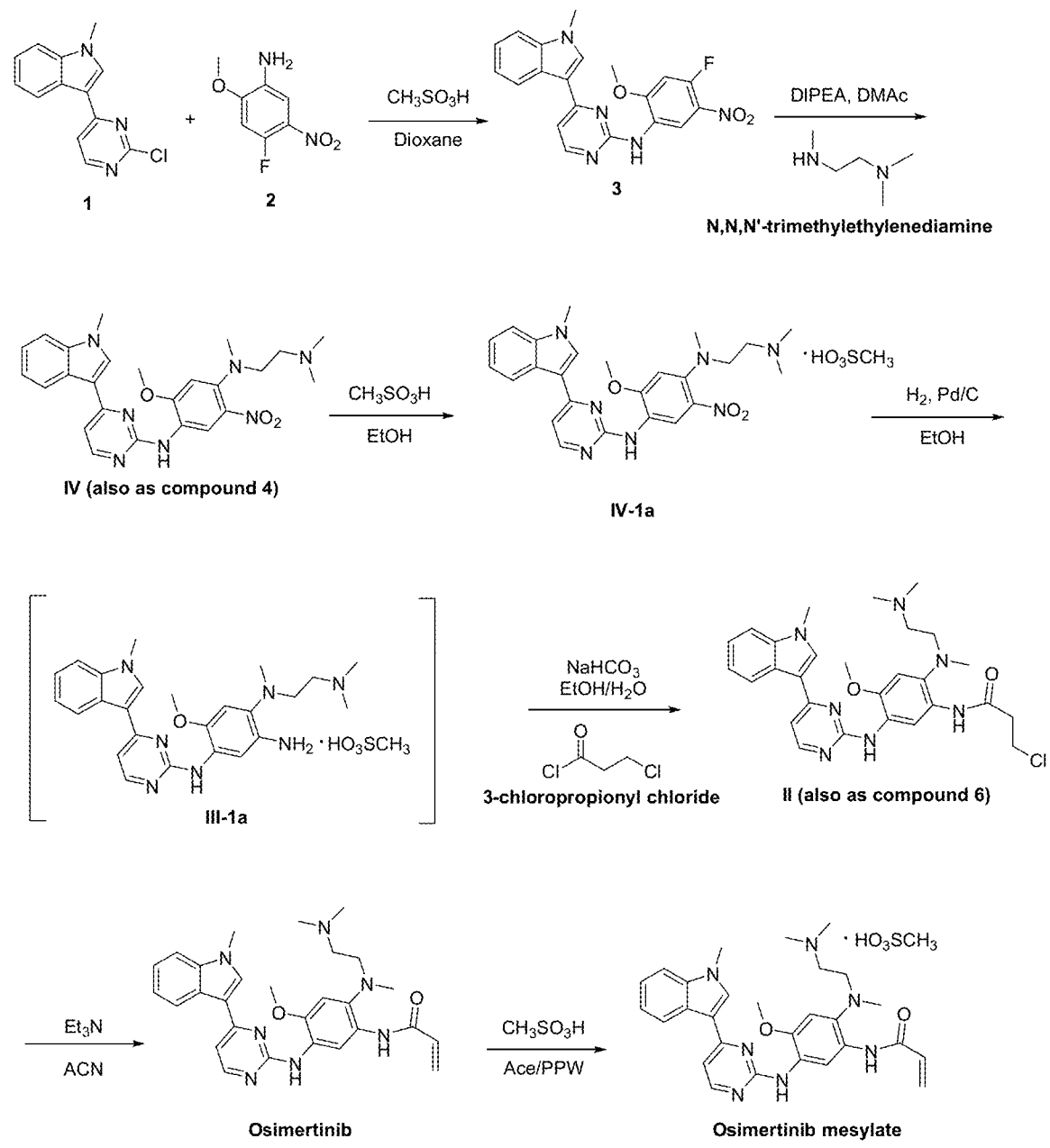
FIG. 4 shows one embodiment of the present disclosure for preparing osimertinib or a mesylate thereof.

More specifically, in one embodiment of the present disclosure, as shown in Scheme 4 of FIG. 4, the improved synthetic process involves the hydrogenation of the mesylate salt of formula (IV-1a) to afford the mesylate salt of formula (III-1a), which is then directly subjected to amidation in ethanol and water as co-solvent to give the amide product of formula (II) (i.e., compound 6) without the isolation of the unstable intermediate of formula (III-1a). This two-step, one-pot process has provided the compound of formula (II) in a high purity as well as in an excellent yield. In the meantime, this two-step, one-pot process has also streamlined the work-up procedure. After amidation, elimination, and salt formation, osimertinib mesylate was obtained in a purity of 99.87% and an overall yield of 77% in four (4) steps from the compound of formula (IV) (i.e., compound 4) in a large-scale production.

The most crucial steps in the preparation of osimertinib and its mesylate salt are 1) the reduction of a nitro group in the compound of formula (IV) (i.e., compound 4) or formula (IV-a); and 2) the formation of an amide bond to form the compound formula (II) (i.e., compound 6). Previously established protocol for the reduction of the nitro group, for example in WO 2013/014448 A1, requires the use of iron as stoichiometric reductant, which not only generates significant waste for scale-up production but also complicates the purification procedure. Furthermore, a typical protocol, such as in both WO 2013/014448 A1 and WO 2017/134051 A1, demands the isolation of the reduced aniline product of compound 5. This aniline intermediate is however extremely unstable under air due to its electron-rich nature. As a consequence, a special care is necessary for its isolation but unfortunately may still lead to diminished yields.

The present invention removes the necessity of isolating the aniline intermediate (compound 5 or formula (III-1a)). Instead, the present process enables the direct coupling to form the amide product of formula (II) (i.e., compound 6). Moreover, water is added to this system as a co-solvent, which not only decreases the amount of impurities formed but also provides a reaction condition that is much easier to work with. Accordingly, the utilization of the mesylate salt of the nitro compound of formula (IV-1a) as the starting material offers better stability for compound storage, as compared to the corresponding free form of formula (IV) (i.e., compound 4). Applicant has also surprisingly discovered that, the hydrogenation of mesylate salt of formula (IV-1a) can be carried out successfully under heterogeneous conditions in a suitable organic solvent, where water is absent. As a result, with all the above-mentioned merits, this two-step, one-pot process provides an overall yield of 97.6% (from the compound of formula (IV-1a) to the compound of formula (II)), which represents a significant improvement over the best known approach.

II. Definitions

"Alkyl" refers to a straight or branched, saturated, aliphatic radical having the number of carbon atoms indicated (i.e., $C_{1-4}$ means one to four carbons). Alkyl can include any number of carbons, such as $C_{1-2}$, $C_{1-3}$, $C_{1-4}$, $C_{2-3}$, $C_{2-4}$, and $C_{3-4}$. For example, $C_{1-4}$ alkyl includes, but is not limited to, methyl, ethyl, propyl, isopropyl, butyl, isobutyl, sec-butyl, and tert-butyl.

"Mesylate" or "mesylate salt" refers to a salt formed from methanesulfonic acid ($CH_3SO_3H$ or abbreviated as MsOH).

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Hydrogenating" refers to the reduction reaction which results in an addition of hydrogen (usually as $H_2$). If an organic compound is hydrogenated, it becomes more "saturated" with hydrogen atoms. The reaction typically requires the use of a catalyst.

"Amidating" refers to the reaction which results in the formation of an amide.

"Catalyst" refers to a substance that increases the rate of a chemical reaction by reducing the activation energy, but which is left unchanged by the reaction. Catalysts may be classified as either homogeneous or heterogeneous. A homogeneous catalyst is one whose molecules are dispersed in the same phase as the reactant molecules. A heterogeneous catalyst is one whose molecules are not in the same phase as the reactants, which are typically gases or liquids that are adsorbed onto the surface of the solid catalyst. Catalysts useful in the present invention are both homogeneous catalysts and heterogeneous catalysts.

"Metal" refers to elements of the periodic table that are metallic and that can be neutral, or positively charged as a result of having more or fewer electrons in the valence shell than is present for the neutral metallic element. Metals useful in the present invention include the alkali metals and transition metals. Alkali metals in the present invention include alkali metal cations. Alkali metal cations useful in the present invention include $Li^+$, $Na^+$, $K^+$, and $Cs^+$. Transition metals useful in the present invention include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac.

"Transition-metal catalyst" refers to a compound that is composed of a transition metal as defined herein that can be neutral or positively charged.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, methyltetrahydrofuran, diethyl ether, 1,4-dioxane, acetone, ethyl acetate, dimethylformamide, acetonitrile, dimethyl sulfoxide, and N-methylpyrrolidone. Representative non-polar solvents include alkanes (pentanes, hexanes, etc.), cycloalkanes (cyclopentane, cyclohexane, etc.), benzene, and toluene. Other solvents are useful in the present invention.

"Organic solvent" refers to water-miscible or -immiscible solvents capable of dissolving either or both of water-soluble and water-insoluble organic compounds.

"Aprotic solvent" refers to solvents that lack an acidic hydrogen. Consequently, they are not hydrogen bond donors. Common characteristics of aprotic solvents are solvents that can accept hydrogen bonds, solvents do not have acidic hydrogen, and solvents dissolve salts. Examples of aprotic solvents include, but are not limited to, N-methylpyrrolidone (NMP), tetrahydrofuran (THF), 2-methyl tetrahydrofuran (MeTHF), ethyl acetate (EtOAc), acetone, dimethylformamide (DMF), acetonitrile (MeCN), dimethyl sulfoxide (DMSO), propylene carbonate (PC), and hexamethylphosphoramide (HMPA).

"Base" refers to a functional group that deprotonates water to produce a hydroxide ion. Bases useful in the present invention include organic bases and inorganic bases. Exemplary organic bases include amines as defined herein. Exemplary inorganic bases include alkali bicarbonates, alkali carbonates, alkali phosphates tribasic, and alkali phosphate dibasic, as defined herein. Amines useful in the present invention as bases include tertiary amines as defined herein.

"Tertiary amine" refers to a compound having formula $N(R)_3$ wherein the R groups can be alkyl, aryl, heteroalkyl, heteroaryl, among others, or two R groups together form a N-linked heterocycloalkyl. The R groups can be the same or different. Non-limiting examples of tertiary amines include triethylamine, tri-n-butylamine, N,N-diisopropylethylamine, N-methylpyrrolidine, N-methylmorpholine, dimethylaniline, diethylaniline, 1,8-bis(dimethylamino)naphthalene, quinuclidine, and 1,4-diazabicylo[2.2.2]-octane (DABCO).

"Alkali bicarbonate" refers to a class of chemical compounds which are composed of an alkali metal cation and the hydrogencarbonate anion ($HCO_3^-$). Alkali carbonates useful in the present invention include lithium bicarbonate ($LiHCO_3$), sodium bicarbonate ($NaHCO_3$), potassium bicarbonate ($KHCO_3$), and cesium bicarbonate ($CsHCO_3$).

"Alkali carbonate" refers to a class of chemical compounds which are composed of an alkali metal cation and the carbonate anion ($CO_3^{2-}$). Alkali carbonates useful in the present invention include lithium carbonate ($Li_2CO_3$), sodium carbonate ($Na_2CO_3$), potassium carbonate ($K_2CO_3$), and cesium carbonate ($Cs_2CO_3$).

"Alkali phosphate tribasic" refers to a class of chemical compounds which are composed of an alkali metal cation and the phosphate anion ($PO_4^{3-}$). Alkali phosphates tribasic useful in the present invention include sodium phosphate tribasic ($Na_3PO_4$) and potassium phosphate tribasic ($K_3PO_4$).

"Alkali phosphate dibasic" refers to a class of chemical compounds which are composed of an alkali metal cation and the hydrogenphosphate anion ($HPO_4^{2-}$). Alkali phosphates dibasic useful in the present invention include sodium phosphate dibasic ($Na_2HPO_4$) and potassium phosphate dibasic ($K_2HPO_4$).

"Isolating" refers to the separation (an element or compound) in pure form from substances with which it is combined or mixed.

III. Processes

In a first aspect, the present disclosure provides a process for preparing osimertinib represented by formula (I):

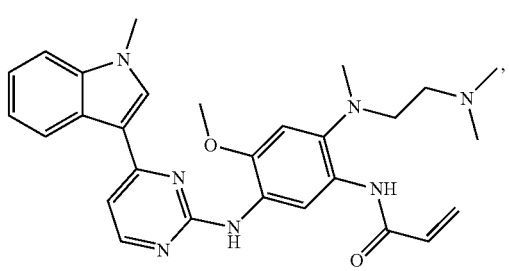

or a salt thereof, the process including:

2a) contacting a compound represented by formula (IV-1):

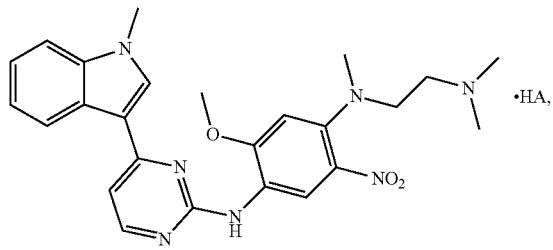

(IV-1)

with a hydrogen source and a transition-metal catalyst in a first solvent to form a compound represented by formula (III):

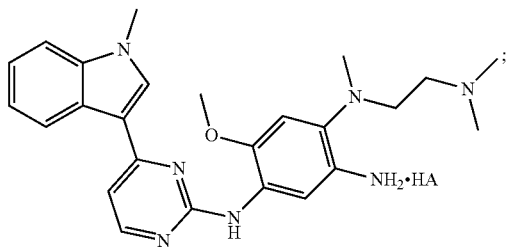

(III)

2b) reacting the compound of formula (III) with 3-chloropropionyl chloride and a first base to form a compound represented by formula (II):

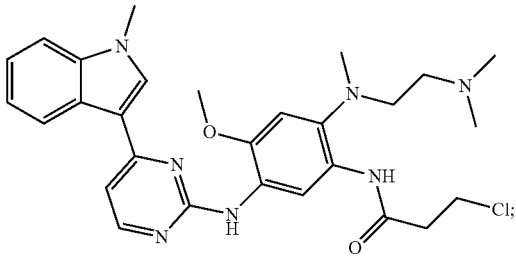

(II)

3) converting the compound of formula (II) to osimertinib of formula (I); and
4) optionally converting osimertinib of formula (I) to a salt thereof, wherein HA is an acid addition salt in each of the compound of formula (III) and the compound of formula (IV-1); and steps 2a) and 2b) are conducted in one-pot.

Acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

In some embodiments, HA in each of the compound of formula (III) and the compound of formula (IV-1) is methanesulfonic acid ($CH_3SO_3H$).

The hydrogen source in step 2a) can be a hydrogen gas or can be generated in situ. In some embodiments, the hydrogen source is a hydrogen gas.

The transition-metal catalyst in step 2a) can be composed of a neutral transition metal (i.e, with zero charge). In some embodiments, the transition metal catalyst is Ni(0), Pd(0), or Pt(0), each of which is optionally on carbon. In some embodiments, the transition metal catalyst is Ni(0) on carbon, Pd(0) on carbon, or Pt(0) on carbon. In some embodiments, the transition metal catalyst includes Pd(0) on carbon. In some embodiments, the transition metal catalyst is Pd(0) on carbon.

The first solvent in step 2a) can be any suitable organic solvent as defined herein. In some embodiments, the first solvent is an alcohol. In some embodiments, the first solvent is $C_{1-4}$ alkyl alcohol. In some embodiments, the first solvent includes ethanol. In some embodiments, the first solvent is ethanol.

The reaction of step 2a) can be conducted in the absence of water. In some embodiments, a reaction mixture of step 2a) is substantially free of water.

In general, the hydrogenating reaction of step 2a) can be conducted at any suitable temperature. In some embodiments, the hydrogenating reaction is conducted at a temperature of no less than 30° C. In some embodiments, the hydrogenating reaction is conducted at a temperature of from about 40° C. to about 50° C. In some embodiments, the hydrogenating reaction is conducted at a temperature of about 45° C.

After the completion of the reaction of step 2a), the transition-metal catalyst can be removed from the reaction mixture by filtration. In some embodiments, the transition-metal catalyst is removed by filtration. In some embodiments, Pd(0) on carbon is removed by filtration.

The compound of formula (III) from step 2a) can be used directly for the next step without isolation and/or purification. In some embodiments, the compound of formula (III) from step 2a) is directly used in step 2b) without isolation. In some embodiments, the compound of formula (III) from step 2a) is directly used in step 2b) without purification. In some embodiments, the compound of formula (III) from step 2a) is directly used in step 2b) without isolation and purification.

The amidating reaction of step 2b) can be conducted in a solvent including the first solvent. In some embodiments, step 2b) includes the first solvent. In some embodiments, step 2b) includes the first solvent and water. In some embodiments, step 2b) includes $C_{1-4}$ alkyl alcohol and water. In some embodiments, step 2b) includes ethanol and water.

The base in step 2b) can be any suitable base including amines and inorganic bases as defined herein. Exemplary inorganic bases include alkali bicarbonates, alkali carbonates, alkali phosphates tribasic, and alkali phosphate dibasic, as defined herein. In some embodiments, the base is an alkali bicarbonate. In some embodiments, the base is lithium bicarbonate ($LiHCO_3$), sodium bicarbonate ($NaHCO_3$), potassium bicarbonate (KHCO₃), and cesium bicarbonate (CsHCO₃). In some embodiments, the base is sodium bicarbonate (NaHCO₃).

In general, the amidating reaction of step 2b) can be conducted at any suitable temperature. In some embodiments, the amidating reaction is conducted at a temperature of no more than 10° C. In some embodiments, the amidating reaction is conducted at a temperature of from about 0° C. to about 10° C.

In some embodiments, step 4) is present. In some embodiments, the process includes: 4) converting osimertinib of formula (I) to a mesylate salt thereof.

In some embodiments, the process further includes prior to step 2a):

1) contacting a compound of formula (IV):

(IV)

with an acid of HA in a second solvent to form the compound of formula (IV-1).

The acid of HA can be an acid as described above for forming the acid addition salts. In some embodiments, the acid of HA is methanesulfonic acid (CH₃SO₃H).

The second solvent in step 1) can be any suitable organic solvent as defined herein. In some embodiments, the second solvent is an alcohol. In some embodiments, the second solvent is C₁₋₄ alkyl alcohol. In some embodiments, the second solvent includes ethanol. In some embodiments, the second solvent is ethanol.

With respect to the process as described above, in some embodiments, the compound of formula (IV-1) is a compound represented by formula (IV-1a):

(IV-1a)

With respect to the process as described above, in some embodiments, the compound of formula (III) is a compound represented by formula (III-1a):

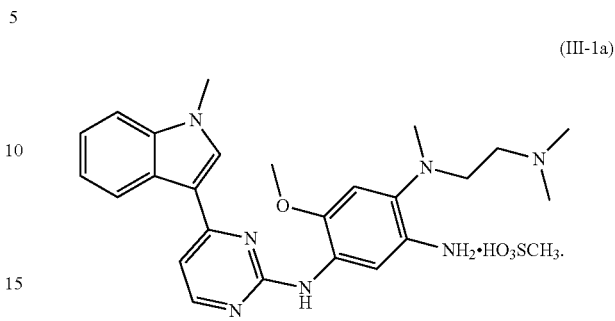

(III-1a)

In a second aspect, the present disclosure provides a process for preparing osimertinib represented by formula (I):

(I)

or a mesylate salt thereof, the process including:

1) contacting a compound of formula (IV):

(IV)

with CH₃SO₃H in ethanol to form a compound represented by formula (IV-1a):

(IV-1a)

2a) hydrogenating the compound of formula (IV-1a) with a hydrogen gas and Pd(0) on carbon in ethanol to form a compound represented by formula (III-1a):

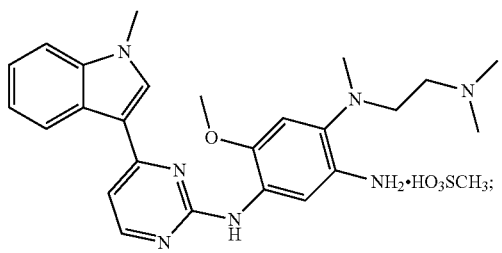

(III-1a)

2b) reacting the compound of formula (III-1a) with 3-chloropropionyl chloride and NaHCO$_3$ in ethanol and water to form a compound represented by formula (II):

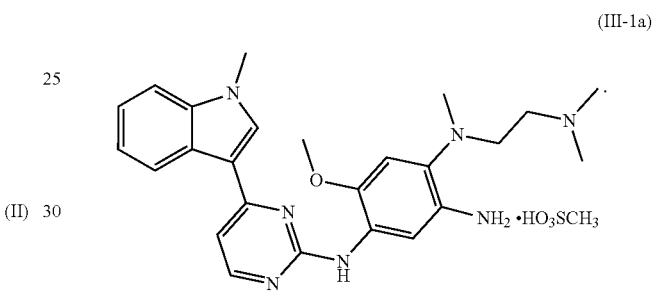

(II)

3) treating the compound of formula (II) with trimethylamine in acetonitrile to provide osimertinib of formula (I); and 4) optionally converting osimertinib of formula (I) with CH$_3$SO$_3$H to a mesylate salt thereof, wherein steps 2a) and 2b) are conducted in one-pot.

In some embodiments, the compound of formula (III-1a) from step 2a) is directly used in step 2b) without isolation. In some embodiments, the compound of formula (III-1a) from step 2a) is directly used in step 2b) without purification. In some embodiments, the compound of formula (III-1a) from step 2a) is directly used in step 2b) without isolation and purification.

After the completion of step 2a), in some embodiments, Pd(0) on carbon is removed by filtration.

In some embodiments, step 4) is present.

While a complete synthetic scheme is provided in the description of the embodiments (as shown in Scheme 4 of FIG. 4), one of skill in the art will appreciate that selected steps of the instant process can be performed independent of the origin of the starting material or intermediates.

IV. Compounds

In a third aspect, the present disclosure provides a compound, represented by formula (IV-1a):

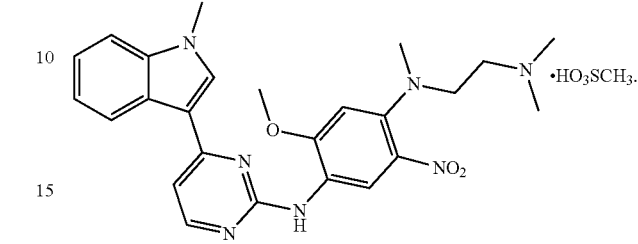

(IV-1a)

In a fourth aspect, the present disclosure provides a compound, represented by formula (III-1a):

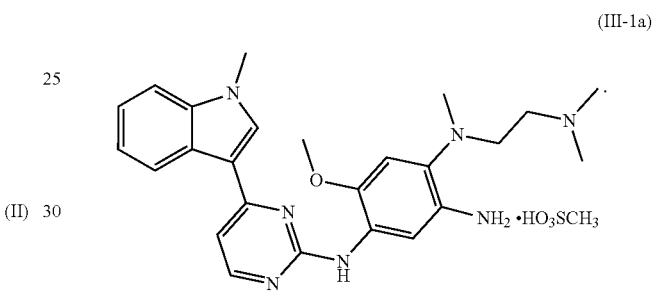

(III-1a)

V. Examples

The following examples are provided to further illustrate but not to limit this invention.

Example 1: Preparation of N-(4-fluoro-2-methoxy-5-nitrophenyl)-4-(1-methyl-1H-indol-3-yl)-2-pyrimidinamine (Compound 3)

A mixture of 3-(2-chloro-4-pyrimidinyl)-1-methyl-1H-indole (compound 1) (2.50 kg, 10.26 mol), 4-fluoro-2-methoxy-5-nitroaniline (compound 2) (1.91 kg, 10.26 mol), methanesulfonic acid (1.18 kg, 12.28 mol), and 1,4-dioxane (42.5 L) were heated to 80° C. and stirred for 5 hours. DTPEA (2.92 kg, 22.60 mol) was added. The resulting mixture was filtered and then dried under vacuum to give N-(4-fluoro-2-methoxy-5-nitrophenyl)-4-(1-methyl-1H-indol-3-yl)-2-pyrimidinamine (compound 3) (3.67 kg, 89.7% yield).

Example 2: Preparation of N1-(2-(dimethylamino)ethyl)-5-methoxy-N1-methyl-N4-(4-(1-methyl-1H-indol-3-yl)pyrimidin-2-yl)-2-nitrobenzene-1,4-diamine (IV) (i.e., Compound 4)

A mixture of N-(4-fluoro-2-methoxy-5-nitrophenyl)-4-(1-methyl-1H-indol-3-yl)-2-pyrimidinamine (compound 3) (1.80 kg, 4.58 mol), N,N,N'-trimethyl-1,2-ethanediamine (0.61 kg, 6.00 mol), DIPEA (0.77 kg, 5.96 mol), and DMAc (12.6 L) were heated to 80° C. and stirred for 5 hours. A NaOH aqueous solution was added. The resulting mixture was filtered and then dried under vacuum to give N1-(2-(dimethylamino)ethyl)-5-methoxy-N1-methyl-N4-(4-(1-methyl-1H-indol-3-yl)pyrimidin-2-yl)-2-nitrobenzene-1,4-diamine (IV, compound 4) (2.12 kg, 97.4% yield).

Example 3: Preparation of N1-(2-(dimethylamino) ethyl)-5-methoxy-N1-methyl-N4-(4-(1-methyl-1H-indol-3-yl)pyrimidin-2-yl)-2-nitrobenzene-1,4-diamine (IV-1a)

A mixture of N1-(2-(dimethylamino)ethyl)-5-methoxy-N1-methyl-N4-(4-(1-methyl-1H-indol-3-yl)pyrimidin-2-yl)-2-nitrobenzene-1,4-diamine (IV, compound 4) (2.00 kg, 4.21 mmol) and EtOH (16.0 L) were heated to 45° C. and added a solution of MsOH (0.40 kg, 0.27 L) in EtOH (4.0 L). The resulting mixture was allowed to cool to room temperature before filtered and then dried under vacuum to give N1-(2-(dimethylamino)ethyl)-5-methoxy-N1-methyl-N4-(4-(1-methyl-1H-indol-3-yl)pyrimidin-2-yl)-2-nitrobenzene-1,4-diamine mesylate salt (IV-1a) (2.30 kg 93.0% yield).

Example 4: Preparation of 3-chloro-N-(2-((2-(dimethylamino)ethyl)methylamino)-4-methoxy-5-((4-(1-methyl-1H-indol-3-yl)pyrimidin-2-yl)amino)phenyl) propanamide (II) (i.e., Compound 6)

A mixture of N1-(2-(dimethylamino)ethyl)-5-methoxy-N1-methyl-N4-(4-(1-methyl-1H-indol-3-yl)pyrimidin-2-yl)-2-nitrobenzene-1,4-diamine mesylate salt (IV-1a) (0.210 kg, 367.4 mmol), 10% Pd/C (6.3 g) and EtOH (1470 mL) was hydrogenated under $H_2$ at 45° C. for 13 hours. $H_2O$ was added to the solution, and the mixture was filtered through Celite. The Celite layer was washed with EtOH/$H_2O$ to obtain N1-(2-(dimethylamino)ethyl)-5-methoxy-N1-methyl-N4-(4-(1-methyl-1H-indol-3-yl)pyrimidin-2-yl)benzene-1,2,4-triamine (III-1a) solution. To the compound (III-1a) solution were added 3-chloropropionyl chloride (60.6 g, 477.6 mmol), acetone, and NaHCO$_3$ aqueous solution under cooling condition. The resulting mixture was filtered and dried under vacuum to obtain 3-chloro-N-(2-((2-(dimethylamino)ethyl)methylamino)-4-methoxy-5-((4-(1-methyl-1H-indol-3-yl)pyrimidin-2-yl)amino)phenyl)propanamide (II, compound 6) (0.212 kg, 97.6% yield).

Example 5: Preparation of Osimertinib

A mixture of 3-chloro-N-(2-((2-(dimethylamino)ethyl)methylamino)-4-methoxy-5-((4-(1-methyl-1H-indol-3-yl)pyrimidin-2-yl)amino)phenyl)propanamide (II, compound 6) (93.96 g, 163.0 mmol) in acetonitrile (940 mL) and Et$_3$N (49.48 g, 489.0 mmol) were heated to reflux and stirred at this temperature. After the reaction was completed, the reaction mixture was cooled to 20-30° C. To the resulting mixture was added water. The solids were filtered and then dried under vacuum to obtain osimertinib (75.13 g, 85.80% yield).

Example 6: Preparation of Osimertinib Mesylate

Osimertinib (10 g, 20 mmol) was reacted with MsOH (1.92 g, 20.00 mmol) in acetone (103.4 mL) and water (10 mL) at 50° C. The solid was collected by filtration and then dried under vacuum to give osimertinib mesylate (11.46 g with 96% yield).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing osimertinib represented by formula (I):

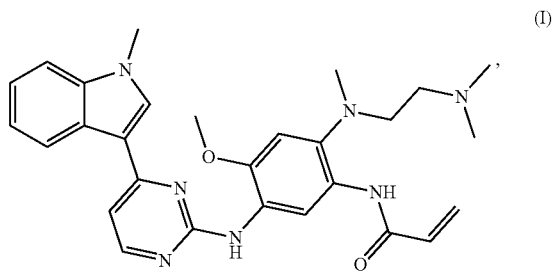 [SMILES: C=CC(=O)Nc1cc(Nc2nccc(-c3cn(C)c4ccccc34)n2)c(OC)cc1N(C)CCN(C)C]

or a salt thereof, comprising:

2a) contacting a compound represented by formula (IV-1):

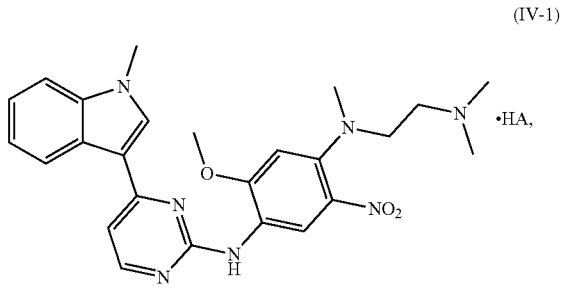 [SMILES: COc1cc(N(C)CCN(C)C)c([N+](=O)[O-])cc1Nc1nccc(-c2cn(C)c3ccccc23)n1]

with a hydrogen source and a transition-metal catalyst selected from the group consisting of Ni(0), Pd(0), and Pt(0), each of which is optionally on carbon in a first organic solvent to form a compound represented by formula (III):

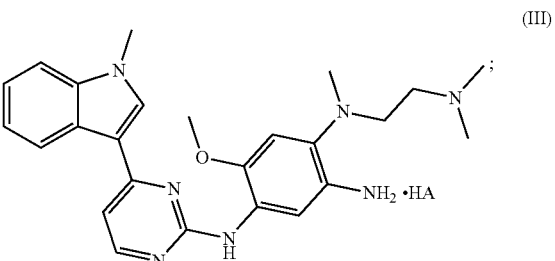

2b) reacting the compound of formula (III) with 3-chloropropionyl chloride and a base to form a compound represented by formula (II):

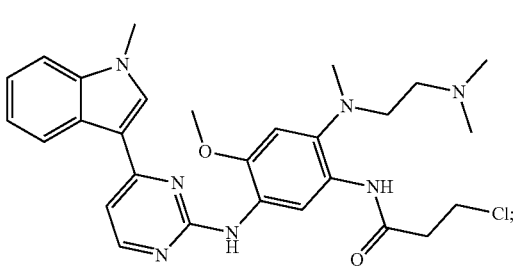

3) Converting the compound of formula (II) to osimertinib of formula (I); and
4) optionally converting osimertinib of formula (I) to a salt thereof, wherein HA is an acid addition salt in each of the compound of formula (III) and the compound of formula (IV-1); and steps 2a) and 2b) are conducted in one-pot.

2. The process of claim 1, wherein HA is $CH_3SO_3H$.

3. The process of claim 1, wherein the hydrogen source in step 2a) is a hydrogen gas.

4. The process of claim 1, wherein the transition-metal catalyst in step 2a) is Pd(0) on carbon.

5. The process of claim 1, wherein the first solvent in step 2a) is $C_{1-4}$ alkyl alcohol.

6. The process of claim 5, wherein the first solvent in step 2a) comprises ethanol.

7. The process of claim 1, wherein a reaction mixture of step 2a) is free of water.

8. The process of claim 1, wherein step 2a) is conducted at a temperature of no less than 30° C.

9. The process of claim 8, wherein step 2a) is conducted at a temperature of from about 40° C. to about 50° C.

10. The process of claim 1, wherein the compound of formula (III) from step 2a) is directly used in step 2b) without isolation.

11. The process of claim 1, wherein step 2b) comprises the first solvent and water.

12. The process of claim 1, wherein the base in step 2b) is an alkali bicarbonate.

13. The process of claim 12, wherein the base in step 2b) is $NaHCO_3$.

14. The process of claim 1, wherein step 2b) is conducted at a temperature of no more than 10° C.

15. The process of claim 14, wherein step 2b) is conducted at a temperature of from about 0° C. to about 10° C.

16. The process of claim 1, wherein, when step 4) is present, converting osimertinib of formula (I) to a mesylate salt thereof.

17. The process of claim 1, further comprising prior to step 2a):
1) Contacting a compound of formula (IV):

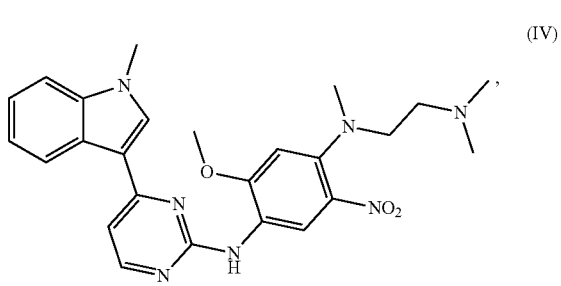 [SMILES: COc1cc(N(C)CCN(C)C)c([N+](=O)[O-])cc1Nc1nccc(-c2cn(C)c3ccccc23)n1]

with an acid of HA in a second solvent to form the compound of formula (IV-1).

18. The process of claim 17, wherein the acid of HA is $CH_3SO_3H$; and the second solvent is $C_{1-4}$ alkyl alcohol.

19. A process for preparing osimertinib represented by formula (I):

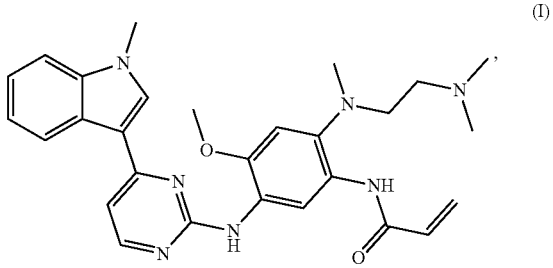 [SMILES: C=CC(=O)Nc1cc(Nc2nccc(-c3cn(C)c4ccccc34)n2)c(OC)cc1N(C)CCN(C)C]

or a mesylate salt thereof, comprising:
1) Contacting a compound of formula (IV):

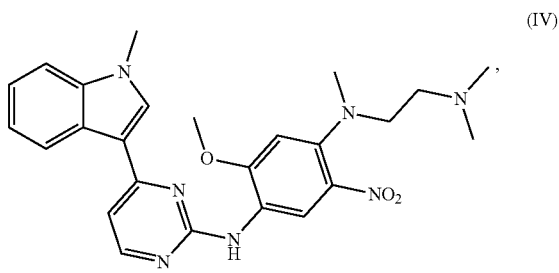 [SMILES: COc1cc(N(C)CCN(C)C)c([N+](=O)[O-])cc1Nc1nccc(-c2cn(C)c3ccccc23)n1]

with CH₃SO₃H in ethanol to form a compound represented by formula (IV-1a):

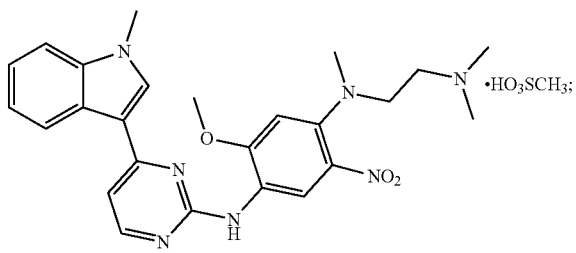

(IV-1a)

2a) hydrogenating the compound of formula (IV-1a) with a hydrogen gas and Pd(0) on carbon in ethanol to form a compound represented by formula (III-1a):

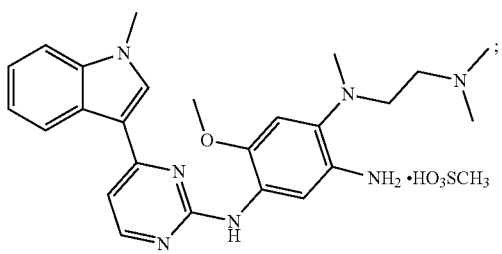

(III-1a)

2b) reacting the compound of formula (III-1a) with 3-chloropropionyl chloride and NaHCO₃ in ethanol and water to form a compound represented by formula (II):

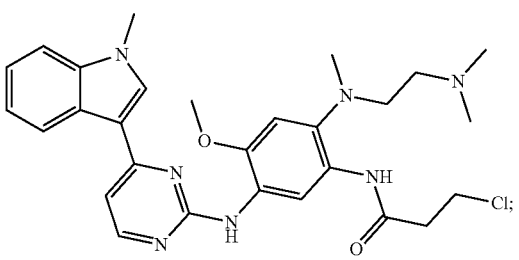

(II)

3) Treating the compound of formula (II) with trimethylamine in acetonitrile to provide osimertinib of formula (I); and 4) optionally converting osimertinib of formula (I) with CH₃SO₃H to a mesylate salt thereof, wherein steps 2a) and 2b) are conducted in one-pot.

\* \* \* \* \*